(12) United States Patent
Thomas, Jr. et al.

(10) Patent No.: US 6,375,929 B1
(45) Date of Patent: Apr. 23, 2002

(54) GENE THERAPY FOR INHIBITION OF ANGIOGENESIS

(75) Inventors: Kenneth A. Thomas, Jr., Chatham Borough, NJ (US); Richard L. Kendall, Doylestown, PA (US); Corey K. Goldman, Birmingham, AL (US); William R. Huckle; Andrew J. Bett, both of Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/427,353

(22) Filed: Oct. 26, 1999

Related U.S. Application Data

(63) Continuation of application No. 08/935,423, filed on Sep. 23, 1997, now abandoned.
(60) Provisional application No. 60/026,641, filed on Sep. 24, 1996.

(51) Int. Cl.$^7$ .................. A61K 49/00; C12N 15/861
(52) U.S. Cl. ............... 424/9.2; 424/93.1; 424/93.2; 424/93.6; 424/9.1; 435/320.1; 435/325
(58) Field of Search .................. 435/320.1, 325; 424/93.1, 93.2, 93.6, 9.1, 9.2

(56) References Cited

U.S. PATENT DOCUMENTS

| | | |
|---|---|---|
| 5,194,596 A | 3/1993 | Tischer et al. |
| 5,240,848 A | 8/1993 | Keck et al. |
| 5,332,671 A | 7/1994 | Ferrara et al. |

OTHER PUBLICATIONS

Eric B. Kmiec, Gene Therapy, American Scientist, vol. 87 pp 240–246 1994.*
J. Go'mez–Navarro et al, Gene Therapy for Cancer, European Journal of Cancer, vol. 35, No. 6, pp 867–885, 1999.*
Potter Wickware, Nature Biotechnology vol. 18, Feb. 2000.*
Charnock–Jones et al. "Identification and Localization of Alternately Splied mRNAs for Vascular Endothelial Growth Factor in Human Uterus and Estrogen Regulation in Endometrial Carcinoma Cell Lines", Biol. Reproduction 48: 1120–1128 (1993).
Ferrara et al. "The Vascular Endothelial Growth Factor Family of Polypeptides", J. Cell. Biochem. 47: 211–218 (1991).
Maglione et al. "Two alternative mRNAs coding for the angiogenic factor, placenta growth factor (P1GF), are transcribed from a single gene of chromosome 12", Oncogene 8: 925–931 (1993).
Hauser et al. "A Heparin–Binding Form of Placenta Growth Factor (P1GF–2) is Expressed in Human Umbilical Vein Endothelial Cells and in Placenta", Growth Factors, vol. 9: 259–268 (1993).
Grimmond et al. "Cloning and Characterization of a Novel Human Gene Related to Vascular Endothelial Growth Factor", Genome Research 6: 124–131 (1996).

Joukov et al. "A novel vascular endothelial growth factor, VEGF–C, is a ligand for the Flt4 (VEGFR–3) and KDR (VEGFR–2) receptor tyrosine kinases", EMBO Jour. vol. 15, No. 2, 290–298 (1996).

Shibuya et al. "Nucleotide sequence and expression of a novel human receptor–type tyrosine kinase gene (flt) closely related to the fms family", Oncogene, 5: 519–524.

Terman et al. "Identification of a new endothelial cell growth factor receptor tyrosine kinase", Oncogene 6: 1677–1683.

Terman et al. "Identification of the KDR Tyrosine Kinase as a Receptor for Vascular Endothelial Cell Growth Factor", Biochemical and Biophysical Research Comm, 187: pp 1579–1586 (1992).

Pajusola et al. "FLT4 Receptor Tyrosine Kinase Contains Seven Immunoglobulin–like Loops and is Expressed in Multiple Human Tissues and Cell Lines", Cancer Res. 52: 5738–5743 (1992).

Kondo et al. "Significance of Vascular Endothelial Growth Factor/Vascular Permeability Factor for Solid Tumor Growth and its Inhibition by the Antibody", Biochemical and Biophysical Research Comm. 194: No. 3 pp1234–1241 (1993).

Kim et al. "The Vascular Endothelial Growth Factor Proteins: Identification of Biologically Relevant Region by Neutralizing Monoclonal Antibodies", Growth Factors, 7: 53–64 (1992).

(List continued on next page.)

Primary Examiner—David Guzo
(74) Attorney, Agent, or Firm—J. Mark Hand; Jack L. Tribble

(57) ABSTRACT

The present invention relates to methods of gene therapy for inhibiting angiogenesis associated with solid tumor growth, tumor metastasis, inflammation, psoriasis, rheumatoid arthritis, hemangiomas, diabetic retinopathy, angiofibromas, and macular degeneration Gene therapy methodology is disclosed for inhibition of primary tumor growth and metastasis by gene transfer of a nucleotide sequence encoding a soluble form of a VEGF tyrosine kinase receptor to a mammalian host. The transferred nucleotide sequence transcribes mRNA and a soluble receptor protein which binds to VEGF in extracellular regions adjacent to the primary tumor and vascular endothelial cells. Formation of a sVEGF-R/VEGF complex will prevent binding of VEGF to the KDR and FLT-1 tyrosine kinase receptors, antagonizing transduction of the normal intracellular signals associated with vascular endothelial cell-induced tumor angiogenesis. In addition, expression of a soluble receptor tyrosine kinase may also impart a therapeutic effect by binding either with or without VEGFs to form non-functional heterodimers with full-length VEGF-specific tyrosine kinase receptors and thereby inhibiting the mitogenic and angiogenic activities of VEGFs.

6 Claims, 8 Drawing Sheets

OTHER PUBLICATIONS

Kim et al. "Inhibition of Vascular Endothelial Growth Factor–Induced Angiogenesis Suppresses Tumour Growth In Vivo", Nature vol. 362, pp841–844 (1993).

Asano et al. "Inhibition of Tumor Growth and Metastasis by an Immunoneutralizing Monoclonal Antibody to Human Vascular Endothelial Growth Factor/Vascular Permeability Factor 121", Cancer Research, 55: 5296–5301.

Carrau et al. "Tumor Angiogenesis as Predictor of Tumor Aggressiveness and Metastic Potential in Squamous Cell Carcinoma of the Head and Neck", Invasion Metastasis 1995: 15: 197–202.

Volm et al. "Interrelationships Between Microvessel Density, Expression of VEGF and Resistance to Doxorubicin of Non–Small Lung Cell Carcinoma", Anticancer Research 16: 213–218 (1996).

Toi et al. "Association of Vascular Endothelial Growth Factor Expression with Tumor Angiogenesis and with Early Relapse in Primary Breast Cancer", Japanese Jour. of Cancer Research 85: 1045–1049 (1994).

Shpitzer et al. "Tumor Angiogenesis as a Prognostic Factor in Early Oral Tongue Cancer", Arch Otolaryngol Head Neck Sug. vol. 122: pp 865–868 (1996).

Giatromanolaki et al., "Prognostic Value of Angiogenesis in Operable Non–Small Cell Lung Cancer", Jour. of Pathology, 179: 80–88 (1996).

Toi et al. "Quantitative Analysis of Vascular Endothelial Growth Factor in Primary Breast Cancer", Cancer, vol. 77, No. 6, pp1101–1106 (1996).

Maeda et al. "Prognostic Value of Vascular Endothelial Growth Factor Expression in Gastric Carcinoma", Cancer, vol. 77, No. 6, pp 858–863 (1996).

Anan et al. "Vascular Endothelial Growth Factor and Platelet–Derived Growth Factor are Potential Angiogenic and Metastic Factors in Human Breast Cancer", Surgery, vol. 119, pp 333–339 (1996).

Chu et al. "Cell Targeting with Retroviral Vector Particles Containing Antibody–Envelope Fusion Proteins", Gene Therapy, vol. 1, pp 292–299 (1994).

Couture et al. "Retroviral Vectors Containing Chimeric Promoter/enhancer Elements Exhibit Cell–Type–Specific Gene Expression", Human Gene Therapy, 5: 667–677 (1994).

Felgner et al. "Enhanced Gene Delivery and Mechanism Studies with a Novel Series of Cationic Lipid Formulations", J. Biol. Chem. 269: 2550–2561 (1994).

Derossi et al. "Internalization of Macromolecules by Live Cells", Restorative Neurology and Neuroscience 8, pp7–10 (1995).

Abdallah et al. "Non–Viral Gene Transfer: Applications in Developmental Biology and Gene Therapy", Biol. Cell 85: pp 1–7 (1995).

Graham et al. "Methods for Constructions of Adenovirus Vectors", Mol. Biotech. 3: 207–220 (1995).

McGrory et al. "Simple Technique for the Rescue of Early Region I Mutations into Infectious Human Adenovirus Type 5", Virology, 163: 614–617 (1988).

Ghosh–Choudhury et al. "Human Adenovirus Cloning Vectors Based on Infectious Bacterial Plasmids", Gene 50: 161–171 (1986).

Mittal et al. "Monitoring foreign gene expression by a human adenovirus based vector usign the firefly luciferase gene as a reporter", Virus Research, 28: 67–90 (1993).

Bett et al. "An efficient and flexible system for construction of adenovirus vectors with insertions or deletions in early regions 1 and 3", Proc. Natl Acad. Sci USA, vol. 91, pp 8802–8806 (1994).

Olofsson et al. "Vascular Endothelial Growth Factor B, A Novel Growth Factor for Endothelial Cells", Proc. Natl. Acad. Sci. USA, vol. 93, pp 2576–2581 (1996).

Yamada et al. "Molecular Cloning of a Novel Vascular Endothelial Growth Factor, VEGF–D", Genomics, 42: 483–388 (1997).

Einerhand et al. "Regulated high–level human B–globin gene expression in erythroid cells following recombinant adeno–associated virus–mediated gene transfer", Gene Therapy, 2: 336–343 (1995).

Staibano et al. "The Prognostic Significance of Tumor Angiogenesis in Nonaggressive and Aggressive Basal Cell Carcinoma of the Human Skin", Human Pathology, 27:695–700.

Kendall et al. "Inhibition of Vascular Endothelial Cell Growth Factor Activity by an Endogenously Encoded Soluble Receptor", Proc. Natl. Acad. Sci. USA, vol. 90, pp 10705–10709, Nov. 1993.

Millauer et al. "Glioblastoma growht inhibited in vivo by a dominant–negative Flk–1 mutant", Nature, 367: 576–579, Feb. 10, 1994.

Aiello et al. "Suppression of retinal neovascularization in vivo by inhibition of vascular endothelial growth factor (VEGF) using soluble VEGF–receptro chimeric proteins", Proc. Natl. Acad. Sci. Vo. 92, pp 10457–10461 Nov. 1995.

Hitt et al. "Techniquest for Human Adenovirus Vector Construction and Characterization", Methods in Molecular Genetics, vol. 7, pp 13–30 (1995).

Fan et al. 'Controlling the vasculature: angiogenesis, anti–angiogenesis and vascular targeting of gene therapy', TIPS, vol. 16, pp 57–66 (1995).

Brody et al. 'Adenovirus–Mediated in Vivo Gene Transfer', Annals of the NY Acad. of Sciences, vol. 716, pp 90–102 (1994).

Orkin et al. Report and Recommendations of the Panel to Assess teh NIH Investment in Research on Gene Therapy, Dec. 7, 1995.

Verma et al. 'Gene Therapy—promised, problems and prospects', Nature, vol. 389, pp 239–242 (1997).

Bacchetti et al. 'Inhibition of cellproliferation by an adenovirus vector expressing the human wild type p53 protein', Inter. J. Oncology, vol. 3, pp 781–788 (1993).

Gura, 'Systems for Identifying New Drugs are Often Faulty', Science, vol. 278, pp 1041–1042 (1997).

Ross et al. 'Gene Therapy in the United States: A five–Year Status Report', Human Gene Therapy, vol. 7, pp 1781–1790 (1996).

Anderson, 'Human gene therapy', Nature, vol. 392, pp 25–30 (1998).

* cited by examiner

```
GCGGACACTC CTCTCGGCTC CTCCCCGGCA GCGGCGGCGG CTCGGAGCGG GCTCCGGGGC    60
TCGGGTGCAG CGGCCAGCGG GCCTGGCGGC GAGGATTACC CGGGGAAGTG GTTGTCTCCT   120
GGCTGGAGCC GCGAGACGGG CGCTCAGGGC GCGGGGCCGG CGGCGGCGAA CGAGAGGACG   180
GACTCTGGCG GCCGGGTCGT TGGCCGGGGG AGCGCGGGCA CCGGGCGAGC AGGCCGCGTC   240
GCGCTCACCA TGGTCAGCTA CTGGGACACC GGGGTCCTGC TGTGCGCGCT GCTCAGCTGT   300
CTGCTTCTCA CAGGATCTAG TTCAGGTTCA AAATTAAAAG ATCCTGAACT GAGTTTAAAA   360
GGCACCCAGC ACATCATGCA AGCAGGCCAG ACACTGCATC TCCAATGCAG GGGGGAAGCA   420
GCCCATAAAT GGTCTTTGCC TGAAATGGTG AGTAAGGAAA GCGAAAGGCT GAGCATAACT   480
AAATCTGCCT GTGGAAGAAA TGGCAAACAA TTCTGCAGTA CTTTAACCTT GAACACAGCT   540
CAAGCAAACC ACACTGGCTT CTACAGCTGC AAATATCTAG CTGTACCTAC TTCAAAGAAG   600
AAGGAAACAG AATCTGCAAT CTATATATTT ATTAGTGATA CAGGTAGACC TTTCGTAGAG   660
ATGTACAGTG AAATCCCCGA AATTATACAC ATGACTGAAG GAAGGGAGCT CGTCATTCCC   720
TGCCGGGTTA CGTCACCTAA CATCACTGTT ACTTTAAAAA AGTTTCCACT TGACACTTTG   780
ATCCCTGATG GAAAACGCAT AATCTGGGAC AGTAGAAAGG GCTTCATCAT ATCAAATGCA   840
ACGTACAAAG AAATAGGGCT TCTGACCTGT GAAGCAACAG TCAATGGGCA TTTGTATAAG   900
ACAAACTATC TCACACATCG ACAAACCAAT ACAATCATAG ATGTCCAAAT AAGCACACCA   960
CGCCCAGTCA AATTACTTAG AGGCCATACT CTTGTCCTCA ATTGTACTGC TACCACTCCC  1020
TTGAACACGA GAGTTCAAAT GACCTGGAGT TACCCTGATG AAAAAAATAA GAGAGCTTCC  1080
GTAAGGCGAC GAATTGACCA AAGCAATTCC CATGCCAACA TATTCTACAG TGTTCTTACT  1140
ATTGACAAAA TGCAGAACAA AGACAAAGGA CTTTATACTT GTCGTGTAAG GAGTGGACCA  1200
TCATTCAAAT CTGTTAACAC CTCAGTGCAT ATATATGATA AAGCATTCAT CACTGTGAAA  1260
CATCGAAAAC AGCAGGTGCT TGAAACCGTA GCTGGCAAGC GGTCTTACCG GCTCTCTATG  1320
AAAGTGAAGG CATTTCCCTC GCCGGAAGTT GTATGGTTAA AAGATGGGTT ACCTGCGACT  1380
GAGAAATCTG CTCGCTATTT GACTCGTGGC TACTCGTTAA TTATCAAGGA CGTAACTGAA  1440
GAGGATGCAG GGAATTATAC AATCTTGCTG AGCATAAAAC AGTCAAATGT GTTTAAAAAC  1500
CTCACTGCCA CTCTAATTGT CAATGTGAAA CCCCAGATTT ACGAAAAGGC CGTGTCATCG  1560
TTTCCAGACC CGGCTCTCTA CCCACTGGGC AGCAGACAAA TCCTGACTTG TACCGCATAT  1620
GGTATCCCTC AACCTACAAT CAAGTGGTTC TGGCACCCCT GTAACCATAA TCATTCCGAA  1680
GCAAGGTGTG ACTTTTGTTC AATAATGAA GAGTCCTTTA TCCTGGATGC TGACAGCAAC  1740
ATGGGAAACA GAATTGAGAG CATCACTCAG CGCATGGCAA TAATAGAAGG AAAGAATAAG  1800
ATGGCTAGCA CCTTGGTTGT GGCTGACTCT AGAATTTCTG GAATCTACAT TTGCATAGCT  1860
TCCAATAAAG TTGGGACTGT GGGAAGAAAC ATAAGCTTTT ATATCACAGA TGTGCCAAAT  1920
GGGTTTCATG TTAACTTGGA AAAAATGCCG ACGGAAGGAG AGGACCTGAA ACTGTCTTGC  1980
ACAGTTAACA AGTTCTTATA CAGAGACGTT ACTTGGATTT TACTGCGGAC AGTTAATAAC  2040
AGAACAATGC ACTACAGTAT TAGCAAGCAA AAAATGGCCA TCACTAAGGA GCACTCCATC  2100
ACTCTTAATC TTACCATCAT GAATGTTTCC CTGCAAGATT CAGGCACCTA TGCCTGCAGA  2160
GCCAGGAATG TATACACAGG GGAAGAAATC CTCCAGAAGA AAGAAATTAC AATCAGAGGT  2220
GAGCACTGCA ACAAAAAGGC TGTTTTCTCT CGGATCTCCA AATTTAAAAG CACAAGGAAT  2280
GATTGTACCA CACAAAGTAA TGTAAAACAT TAA                                2313
```

FIG.2

```
Met Val Ser Tyr Trp Asp Thr Gly Val Leu Leu Cys Ala Leu Leu Ser
 1            5                  10                   15
Cys Leu Leu Leu Thr Gly Ser Ser Ser Gly Ser Lys Leu Lys Asp Pro
             20                  25                  30
Glu Leu Ser Leu Lys Gly Thr Gln His Ile Met Gln Ala Gly Gln Thr
         35                  40                  45
Leu His Leu Gln Cys Arg Gly Glu Ala Ala His Lys Trp Ser Leu Pro
     50                  55                  60
Glu Met Val Ser Lys Glu Ser Glu Arg Leu Ser Ile Thr Lys Ser Ala
65              70                  75                      80
Cys Gly Arg Asn Gly Lys Gln Phe Cys Ser Thr Leu Thr Leu Asn Thr
                 85                  90                  95
Ala Gln Ala Asn His Thr Gly Phe Tyr Ser Cys Lys Tyr Leu Ala Val
             100                 105                 110
Pro Thr Ser Lys Lys Lys Glu Thr Glu Ser Ala Ile Tyr Ile Phe Ile
         115                 120                 125
Ser Asp Thr Gly Arg Pro Phe Val Glu Met Tyr Ser Glu Ile Pro Glu
     130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                 165                 170                 175
Leu Ile Pro Asp Gly Lys Arg Ile Ile Trp Asp Ser Arg Lys Gly Phe
             180                 185                 190
Ile Ile Ser Asn Ala Thr Tyr Lys Glu Ile Gly Leu Leu Thr Cys Glu
         195                 200                 205
Ala Thr Val Asn Gly His Leu Tyr Lys Thr Asn Tyr Leu Thr His Arg
     210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                 245                 250                 255
Pro Leu Asn Thr Arg Val Gln Met Thr Trp Ser Tyr Pro Asp Glu Lys
             260                 265                 270
Asn Lys Arg Ala Ser Val Arg Arg Ile Asp Gln Ser Asn Ser His
         275                 280                 285
Ala Asn Ile Phe Tyr Ser Val Leu Thr Ile Asp Lys Met Gln Asn Lys
     290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                 325                 330                 335
Lys His Arg Lys Gln Gln Val Leu Glu Thr Val Ala Gly Lys Arg Ser
             340                 345                 350
Tyr Arg Leu Ser Met Lys Val Lys Ala Phe Pro Ser Pro Glu Val Val
         355                 360                 365
Trp Leu Lys Asp Gly Leu Pro Ala Thr Glu Lys Ser Ala Arg Tyr Leu
     370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                 405                 410                 415
Asn Leu Thr Ala Thr Leu Ile Val Asn Val Lys Pro Gln Ile Tyr Glu
             420                 425                 430
Lys Ala Val Ser Ser Phe Pro Asp Pro Ala Leu Tyr Pro Leu Gly Ser
         435                 440                 445
Arg Gln Ile Leu Thr Cys Thr Ala Tyr Gly Ile Pro Gln Pro Thr Ile
     450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                 485                 490                 495
```

FIG. 3A

```
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
            565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
            645                 650                 655
Gly Glu His Cys Asn Lys Lys Ala Val Phe Ser Arg Ile Ser Lys Phe
            660                 665                 670
Lys Ser Thr Arg Asn Asp Cys Thr Thr Gln Ser Asn Val Lys His
        675                 680                 685
```

FIG. 3B

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 2313 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
GCGGACACTC CTCTCGGCTC CTCCCCGGCA GCGGCGGCGG CTCGGAGCGG GCTCCGGGGC    60
TCGGGTGCAG CGGCCAGCGG GCCTGGCGGC GAGGATTACC CGGGGAAGTG GTTGTCTCCT   120
GGCTGGAGCC GCGAGACGGG CGCTCAGGGC GCGGGGCCGG CGGCGGCGAA CGAGAGGACG   180
GACTCTGGCG GCCGGGTCGT TGGCCGGGGG AGCGCGGGCA CCGGGCGAGC AGGCCGCGTC   240
GCGCTCACCA TGGTCAGCTA CTGGGACACC GGGGTCCTGC TGTGCGCGCT GCTCAGCTGT   300
CTGCTTCTCA CAGGATCTAG TTCAGGTTCA AAATTAAAAG ATCCTGAACT GAGTTTAAAA   360
GGCACCCAGC ACATCATGCA AGCAGGCCAG ACACTGCATC TCCAATGCAG GGGGGAAGCA   420
GCCCATAAAT GGTCTTTGCC TGAAATGGTG AGTAAGGAAA GCGAAAGGCT GAGCATAACT   480
AAATCTGCCT GTGGAAGAAA TGGCAAACAA TTCTGCAGTA CTTTAACCTT GAACACAGCT   540
CAAGCAAACC ACACTGGCTT CTACAGCTGC AAATATCTAG CTGTACCTAC TTCAAAGAAG   600
AAGGAAACAG AATCTGCAAT CTATATATTT ATTAGTGATA CAGGTAGACC TTTCGTAGAG   660
ATGTACAGTG AAATCCCCGA AATTATACAC ATGACTGAAG GAAGGGAGCT CGTCATTCCC   720
TGCCGGGTTA CGTCACCTAA CATCACTGTT ACTTTAAAAA AGTTTCCACT TGACACTTTG   780
ATCCCTGATG GAAAACGCAT AATCTGGGAC AGTAGAAAGG GCTTCATCAT ATCAAATGCA   840
ACGTACAAAG AAATAGGGCT TCTGACCTGT GAAGCAACAG TCAATGGGCA TTTGTATAAG   900
ACAAACTATC TCACACATCG ACAAACCAAT ACAATCATAG ATGTCCAAAT AAGCACACCA   960
CGCCCAGTCA AATTACTTAG AGGCCATACT CTTGTCCTCA ATTGTACTGC TACCACTCCC  1020
TTGAACACGA GAGTTCAAAT GACCTGGAGT TACCCTGATG AAAAAAATAA GAGAGCTTCC  1080
GTAAGGCGAC GAATTGACCA AAGCAATTCC CATGCCAACA TATTCTACAG TGTTCTTACT  1140
ATTGACAAAA TGCAGAACAA AGACAAAGGA CTTTATACTT GTCGTGTAAG GAGTGGACCA  1200
TCATTCAAAT CTGTTAACAC CTCAGTGCAT ATATATGATA AAGCATTCAT CACTGTGAAA  1260
CATCGAAAAC AGCAGGTGCT TGAAACCGTA GCTGGCAAGC GGTCTTACCG GCTCTCTATG  1320
AAAGTGAAGG CATTTCCCTC GCCGGAAGTT GTATGGTTAA AAGATGGGTT ACCTGCGACT  1380
GAGAAATCTG CTCGCTATTT GACTCGTGGC TACTCGTTAA TTATCAAGGA CGTAACTGAA  1440
GAGGATGCAG GGAATTATAC AATCTTGCTG AGCATAAAAC AGTCAAATGT GTTTAAAAAC  1500
CTCACTGCCA CTCTAATTGT CAATGTGAAA CCCCAGATTT ACGAAAAGGC CGTGTCATCG  1560
TTTCCAGACC CGGCTCTCTA CCCACTGGGC AGCAGACAAA TCCTGACTTG TACCGCATAT  1620
GGTATCCCTC AACCTACAAT CAAGTGGTTC TGGCACCCCT GTAACCATAA TCATTCCGAA  1680
GCAAGGTGTG ACTTTTGTTC CAATAATGAA GAGTCCTTTA TCCTGGATGC TGACAGCAAC  1740
ATGGGAAACA GAATTGAGAG CATCACTCAG CGCATGGCAA TAATAGAAGG AAAGAATAAG  1800
```

-continued

```
ATGGCTAGCA CCTTGGTTGT GGCTGACTCT AGAATTTCTG GAATCTACAT TTGCATAGCT  1860

TCCAATAAAG TTGGGACTGT GGGAAGAAAC ATAAGCTTTT ATATCACAGA TGTGCCAAAT  1920

GGGTTTCATG TTAACTTGGA AAAAATGCCG ACGGAAGGAG AGGACCTGAA ACTGTCTTGC  1980

ACAGTTAACA AGTTCTTATA CAGAGACGTT ACTTGGATTT TACTGCGGAC AGTTAATAAC  2040

AGAACAATGC ACTACAGTAT TAGCAAGCAA AAAATGGCCA TCACTAAGGA GCACTCCATC  2100

ACTCTTAATC TTACCATCAT GAATGTTTCC CTGCAAGATT CAGGCACCTA TGCCTGCAGA  2160

GCCAGGAATG TATACACAGG GGAAGAAATC CTCCAGAAGA AAGAAATTAC AATCAGAGGT  2220

GAGCACTGCA ACAAAAAGGC TGTTTTCTCT CGGATCTCCA AATTTAAAAG CACAAGGAAT  2280

GATTGTACCA CACAAAGTAA TGTAAAACAT TAA                                2313
```

(2) INFORMATION FOR SEQ ID NO:2:

(i) SEQUENCE CHARACTERISTICS:
        (A) LENGTH: 687 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Met Val Ser Tyr Trp Asp Thr Gly Val Leu Leu Cys Ala Leu Leu Ser
  1               5                  10                  15

Cys Leu Leu Leu Thr Gly Ser Ser Gly Ser Lys Leu Lys Asp Pro
                 20                  25                  30

Glu Leu Ser Leu Lys Gly Thr Gln His Ile Met Gln Ala Gly Gln Thr
                     35                  40                  45

Leu His Leu Gln Cys Arg Gly Glu Ala Ala His Lys Trp Ser Leu Pro
     50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
                115                 120                 125

Ser Asp Thr Gly Arg Pro Phe Val Glu Met Tyr Ser Glu Ile Pro Glu
                130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
```

-continued

```
            210                 215                 220
Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
                260                 265                 270

Asn Lys Arg Ala Ser Val Arg Arg Arg Ile Asp Gln Ser Asn Ser His
            275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
                435                 440                 445

Arg Gln Ile Leu Thr Cys Thr Ala Tyr Gly Ile Pro Gln Pro Thr Ile
                450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
                515                 520                 525

Ile Ser Gly Ile Tyr Ile Cys Ile Ala Ser Asn Lys Val Gly Thr Val
                530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
            610                 615                 620

Asn Val Ser Leu Gln Asp Ser Gly Thr Tyr Ala Cys Arg Ala Arg Asn
625                 630                 635                 640
```

-continued

```
Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
                660                 665                 670

Lys Ser Thr Arg Asn Asp Cys Thr Thr Gln Ser Asn Val Lys His
            675                 680                 685
```

GENE THERAPY FOR INHIBITION OF ANGIOGENESIS

CROSS-REFERENCE TO RELATED APPLICATIONS

This application is a continuation of U.S. application Ser. No. 08/935,423, filed Sep. 23, 1997, now abandoned, which claims benefit under 35 USC 119(e) of U.S. provisional application Ser. No. 60/026,641, filed Sep. 24, 1996.

FIELD OF THE INVENTION

The present invention relates to methods of gene therapy for inhibiting angiogenesis associated with tumor growth, inflammation, psoriasis, rheumatoid arthritis, hemangiomas, diabetic retinopathy, angiofibromas, and macular degeneration.

This invention also relates to animal models useful in the investigation of gene therapy-mediated inhibition of angiogenesis. The invention also relates to recombinant vectors which are useful in the disclosed gene therapy methods.

BACKGROUND OF THE INVENTION

Vascular endothelial cells form a luminal non-thrombogenic monolayer throughout the vascular system. Mitogens promote embryonic vascular development, growth, repair and angiogenesis in these cells. Angiogenesis involves the proteolytic degradation of the basement membrane on which endothelial cells reside followed by the subsequent chemotactic migration and mitosis of these cells to support sustained growth of a new capillary shoot. One class of mitogens selective for vascular endothelial cells include vascular endothelial growth factor (referred to as VEGF or VEGF-A) and the homologues placenta growth factor (PlGF), VEGF-B and VEGF-C.

Human VEGF exists as a glycosylated homodimer in one of five mature processed forms containing 206, 189, 165, 145 and 121 amino acids, the most prevalent being the 165 amino acid form.

U.S. Pat. No. 5,240,848 discloses the nucleotide and amino acid sequence encoding the 189 amino acid form of human VEGF.

U.S. Pat. No. 5,332,671 discloses the nucleotide and amino acid sequence encoding the 165 amino acid form of human VEGF.

Charnock-Jones et al (1993, *Biol. Reproduction* 48: 1120–1128) discloses the VEGF145 splice variant m RNA.

U.S. Pat. No. 5,194,596 discloses the nucleotide and amino acid sequence encoding the 121 amino acid form of human VEGF.

The 206 amino acid and 189 amino acid forms of human VEGF each contain a highly basic 24-amino acid insert that promotes tight binding to heparin, and presumably, heparin proteoglycans on cellular surfaces and within extracellular matrices (Ferrara, et al., 1991, *J. Cell. Biochem.* 47: 211–218). The $VEGF_{165}$ form binds heparin to a lesser extent while $VEGF_{121}$ does not bind heparin.

Human PlGF is also a glycosylated homodimer which shares 46% homology with VEGF at the protein level. Differential splicing of human PlGF mRNA leads to either a 170 amino acid or 149 amino acid precursor, which are proteolytically processed to mature forms of 152 or 131 amino acids in length, respectively (Maglione, et al., 1993, *Oncogene* 8: 925–931; Hauser and Weich, 1993, *Growth Factors* 9: 259–268).

VEGF-B was recently isolated and characterized (Olofsson, et al., 1996, *Proc. Natl. Acad. Sci.* 93: 2576–2581; Grimmond et al., 1996, *Genome Research* 6: 124–131). The full length human cDNAs encode 188 and 207 amino acid precursors wherein the $NH_2$ terminal portions are proteolytically processed to mature forms 167 and 186 amino acids in length. Human VEGF-B expression was found predominantly in heart and skeletal muscle as a disulfide-linked homodimer. However, human VEGF-B may also form a heterodimer with VEGF (id. @ 2580).

VEGF-C has also recently been isolated and characterized (Joukov, et al., 1996, *EMBO J.* 15: 290–298). A cDNA encoding VEGF-C was obtained from a human prostatic adenocarcinoma cell line. A 32 kDa precursor protein is proteolytically processed to generate the mature 23 kDa form, which binds the receptor tyrosine kinase, Flt-4.

VEGF-D was identified in an EST library, the full-length coding region was cloned and recognized to be most homologous to VEGF-C among the VEGF family amino acid sequences (Yamada, et al., 1997, *Genomics* 42:483–488). The human VEGF-D mRNA was shown to be expressed in lung and muscle.

VEGF and its homologies impart activity by binding to vascular endothelial cell plasma membrane-spanning tyrosine kinase receptors which then activates signal transduction and cellular signals. The Flt receptor family is a major tyrosine kinase receptor which binds VEGF with high affinity. At present the fit receptor family includes flt-1 (Shibuya, et al., 1990, *Oncogene* 5: 519–524), KDR/flk-1 (Terman, et al., 1991, *Oncogene* 6: 1677–1683; Terman, et al., 1992, *Biochem. Biophys. Res. Commun.* 187: 1579–1586), and flt-4 (Pajusola, et al., 1992, *Cancer Res.* 52:5738–5743).

The involvement of VEGF in promoting tumor angiogenesis has spawned studies investigating possible antagonists of the process. Both polyclonal (Kondo, et al., 1993, *Biochem. Biophys. Res. Commun.* 194: 1234–1241) and monoclonal (Kim, et al., 1992, *Growth Factors* 7: 53–64; Kim, et al., 1993, *Nature* 362: 841–844) antibodies raised against VEGF have been shown to suppress VEGF activity in vivo. Anti-VEGF antibody strategies to interdict angiogenesis and its attendant tumor are also addressed in Kim et al. (1993, *Nature* 362: 841–844) and Asano et al. (1995, *Cancer Research* 55: 5296–5301).

Kendall and Thomas (1993, *Proc. Natl. Acad. Sci.* 90: 10705–10709) isolated and characterized a cDNA encoding a secreted soluble form of flt-1 from cultured human umbilical vein endothelial cells (HUVEC). The recombinant version of this protein was purified by binding to immobilized heparin. Isolated soluble flt-1 was shown to inhibit VEGF activity in vitro. No suggestion regarding gene transfer protocols were disclosed.

Millauer et al. (1994, *Nature* 367: 576–579) disclose in vivo inhibition of tumor angiogenesis by expression of an artificially generated flk-1 mutant in which the intracellular kinase domain but not the membrane-spanning anchor was deleted. The authors do not forward any teaching or suggestion that a soluble form of a VEGF tyrosine kinase receptor would be useful in gene therapy applications.

Neovascularization of malignant tumors is an integral process contributing to solid tumor growth and neoplastic progression (Kondo et al., 1993, *Biochemical & Biophysical Research Communications* 194: 1234–1241; Carrau et al., 1995, *Invasion & Metastasis* 15: 197–202). In this context, several studies have demonstrated a positive correlation between neovascularization in malignant tumors and poor clinical outcomes (Volm et al., 1996, *Anticancer Research* 16: 213–217; Toi et al., 1994, Japanese Journal of Cancer Research 85: 1045–1049; Shpitzer et al., 1996, *Archives of Otolaryngology—Head & Neck Surgery;* 122: 865–868; Staibano et al., 1996, *Human Pathology* 27: 695–700; Giatromanolaki et al., 1996, *J. of Pathology* 179: 80–88). While the angiogenic process has several mediators, it appears that vascular endothelial growth factor (VEGF) may be a critical growth factor with respect to initiating the cascade of events stimulating new blood vessel formation in several tumor types (Toi et al., 1996, *Cancer* 77: 1101–1106; Maeda et al., 1996, *Cancer* 77: 858–63; Anan et al., 1996, *Surgery* 119: 333–339).

Aiello et al. (1995, Proc. Natl. Acad. Sci. USA 92:10457–10461) disclose genetically engineered chimeric extracellular VEGF receptors to block angiogenesis in non-malignant cells.

Despite recent advances in identifying genes encoding ligands and receptors involved in angiogenesis, no gene therapy application has been forwarded which overcomes the deleterious effect this process has in promoting primary tumor growth and subsequent metastasis. The present invention addresses and meets this need.

SUMMARY OF THE INVENTION

The present invention relates to methods of gene therapy for inhibiting VEGF-induced angiogenesis associated with diseases and disorders including, but not limited to, solid tumor growth, tumor metastasis, inflammation, psoriasis, rheumatoid arthritis, hemangiomas, angiofibromas, diabetic retinopathy, and macular degeneration. These disorders are related in that VEGF acts as a mitogen to stimulate local angiogenesis from vascular endothelial cells which in turns exacerbates the condition.

The present invention relates to gene transfer of a DNA vector and concomitant in vivo expression of a soluble form of a tyrosine receptor kinase (sVEGF-R) within the mammalian host which binds VEGF or a VEGF homologue in and around the localized site of the disorder. The formation of a sVEGF-RA/VEGF complex will inhibit binding of VEGF to the FLT-1 and KDR tyrosine kinase receptors spanning the vascular endothelial cell membrane, thus preventing initiation of the signal transduction stimulating angiogenesis. In addition, expression of sVEGF-R may also impart a therapeutic effect by binding to membrane associated VEGF-Rs. VEGF-Rs are thought to be dimerized by binding dimeric VEGF ligand which in turn allows the receptor intracellular tyrosine kinase domains to transphosphorylate each other generating phosphorylated tyrosine residues that facilitate the subsequent binding and activation of downstream signal transduction proteins. sVEGF-Rs can form heterodimers with full-length VEGF-Rs that, because the sVEGF-Rs are devoid of an intracellular tyrosine kinase region, prevent receptor tyrosine kinase domain transphosphorylation, the initiation of signal transduction and thus VEGF-induced mitogenesis and angiogenesis in a dominant negative manner.

A nucleotide sequence encoding a sVEGF-R for inclusion in a gene therapy vector of the present invention may be chosen from a group of genes encoding tyrosine kinase receptors, namely from the group consisting of sflt-1, flt-1, KDR (also denoted flk-1), and flt-4. The resulting DNA fragment encodes a protein or protein fragment which binds VEGF and/or KDR/flk-1 and inhibits formation of a wild-type, functional VEGF-R/VEGF complex.

A preferred application of the present invention relates to promoting inhibition of solid tumor angiogenesis and metastasis by utilizing the disclosed gene therapy methodology. In particular, methods are disclosed for inhibition of primary tumor growth and metastasis by gene transfer of a nucleotide sequence encoding sVEGF-R to a mammalian host. The transferred nucleotide sequence transcribes mRNA and expresses sVEGF-R such that sVEGF-R binds to VEGF in extracellular regions adjacent to the primary tumor and vascular endothelial cells. Formation of a sVEGF-R/VEGF complex will prevent binding of VEGF to the KDR and FLT-1 tyrosine kinase receptors, antagonizing transduction of the normal intracellular signals associated with vascular endothelial cell-induced tumor angiogenesis. In addition, expression of sFLT-1 may also impart a therapeutic effect by binding either with or without VEGFs to form non-functional heterodimers with full-length VEGF-Rs and thereby inhibiting the mitogenic and angiogenic activities of VEGFs.

In a particular embodiment of the present invention a truncated version of a soluble or transmembrane form of FLT-1 (Shibuya, et al., 1990, *Oncogene* 5: 519–524) is utilized in gene therapy protocols. It will be within the purview of the skilled artisan to generate a sVEGF-R or VEGF-RTMI construct expressing a truncated FLT-1 protein which binds to VEGF, a VEGF homologue and/or dimerizes with a full-length VEGF-R inhibiting its activation on the surface plasma membrane of vascular endothelial cells (FIG. 1). Such a construct may be generated by recombinant DNA techniques known in the art using a DNA fragment encoding a partial or complete amino acid sequence of a FLT receptor. Using recombinant DNA techniques, DNA molecules are constructed which encode at least a portion of the VEGF receptor capable of binding VEGF without stimulating either mitogenesis or angiogenesis. Standard recombinant DNA techniques are used such as those found in Maniatis, et al. (1982, Molecular Cloning: A Laboratory Manual; Cold Spring Harbor Laboratory, Cold Spring Harbor, N.Y.).

In another embodiment of the present invention a mutated version of FLT-1 is generated which is defective in protein kinase activity, namely a FLT-1 protein mutated at or around one or more known active sites for protein kinase activity. A flt-1 construction will express the extracellular domain, transmembrane domain and the mutated portion of the intracellular domain such that the resulting protein at least substantially inhibits related intracellular protein kinase activity.

In a preferred embodiment of the present invention, a naturally expressed alternatively spliced DNA encoding a soluble form of FLT-1 (Kendall and Thomas, 1993, *Proc. Natl. Acad. Sci.* 90: 10705–10709; U.S. application Ser. No. 08/232,538, now U.S. Pat. No. 5,712,380 hereby incorporated by reference; described herein as sVEGF-RI or sFLT-1 and listed as SEQ ID NO:1 (nucleotide sequence) and SEQ NO ID:2 (amino acid sequence) is the template for constructing a gene therapy vector wherein either expressed sFLT-1 or a biologically active truncated form binds VEGF and inhibits complex formation, dimerization and activation of full-length VEGF-Rs, and hence, pathological angiogenesis.

The present invention relates to both viral and non-viral recombinant vectors for delivery to the target hosts. To this end, a preferred non-viral recombinant plasmid described herein is pcDNA3/sflt-1. An especially preferred recombinant plasmid of the present invention is pcDNAIAsFLT-1, as decribed in Example Section 5.

A recombinant adenovirus (Ad) system is preferred for delivery and prolonged expression within target cells proximal to a solid tumor. A particularly useful adenovirus system used in the present invention is described in Example 4.

Any sVEGF-R construct, including but in no way limited to sVEGF-RI and biologically active truncated forms, may be delivered to the mammalian host using a vector or other delivery vehicle. DNA delivery vehicles can include viral vectors such as adenoviruses, adeno-associated viruses, and retroviral vectors. See, for example: Chu et al., 1994, *Gene Therapy* 1: 292–299; Couture et al., 1994, *Hum. Gene Therapy.* 5:, 667–277; and Eiverhand et al., 1995, *Gene Therapy* 2:336–343. Non-viral vectors which are also suitable include naked DNA (see Example Sections 1, 2, 3, and 5), DNA-lipid complexes, for example liposome-mediated or ligand/poly-L-Lysine conjugates, such as asialoglycoprotein-mediated delivery systems. See for example: Felgner et al., 1994, *J. Biol. Chem.* 269:2550–2561; Derossi et al., 1995, *Restor. Neurol. Neuros.* 8:7–10; and Abcallah et al., 1995, *Biol. Cell* 85:1–7. It is preferred that local cells such as adipose tissue cells or smooth muscle cells, as well as tumor cells, be targeted for delivery and concomitant in vivo expression of the respective sVEGF-R protein to promote inhibition of tumor angiogenesis.

A recombinant Ad/sVEGF-RI is a preferred virus for targeting cells proximal to a solid tumor.

An especially preferred recombinant Ad/sVEGF-RI virus is AdHCMVsFLT-1.

Another especially preferred recombinant Ad/sVEGF-RI virus is AdHCMVI1sFLT.

Any membrane bound (mVEGF-R) construct or any FLT-1 or KDR construct encoding a protein deficient in kinase activity may be targeted primarily to vascular endothelial cells in the vicinity of tumor growth. DNA delivery vehicles described above may be utilized to target any such gene transfer construct to vascular endothelial cells of the mammalian host.

As used herein, "VEGF" or "VEFG-A" refers to vascular endothelial growth factor.

As used herein, "homologue of VEGF" refers to homodimers of VEGF-B, VEGF-C, VEGF-D and PlGF and any functional heterodimers formed between VEGF-A, VEGF-B, VEGF-C, VEGF-D and PlGF, including but not limited to a VEGF-A/PlGF heterodimer.

As used herein, "VEGF-B" refers to vascular endothelial growth factor-B.

As used herein, "VEGF-C" refers to vascular endothelial growth factor-C.

As used herein, "VEGF-D" refers to vascular endothelial growth factor-D.

As used herein, "KDR" or "FLK-1" refers to kinase insert domain-containing receptor or fetal liver kinase.

As used herein, "FLT-1" refers to fms-like tyrosine linase receptor.

As used herein, "Ad" refers to adenovirus.

As used herein, "HUVEC" refers to human umbilical vein endothelial cell(s).

As used herein, the term "mammalian host" refers to any mammal, including a human being.

As used herein, "sVEGF-R" generically refers to a soluble form of a tyrosine kinase receptor which binds to its respective vascular endothelial growth factor such as VEGF, VEGF-B, VEGF-C, VEGF-D and PlGF without stimulating receptor activation, mitogenesis of vascular endothelial cells or angiogenesis.

As used herein, "sVEGF-RI" or "sFLT-1" refers to the native human soluble form of sFLT, disclosed in U.S. application Ser. No. 08/232,538 and presented herein in cDNA form (comprising SEQ ID NO:1) and protein form (SEQ ID NO:2).

As used herein, "VEGF-Rs" refers to a human wild-type VEGF/VEGF homologue specific tyrosine kinase receptor such as FLT-1 and KDR.

As used herein, "mVEGF-R" generically refers to a human wild-type VEGF/VEGF homologue specific tyrosine kinase receptor such which is membrane bound, including but not limited to FLT-1, VEGF-RTMI, KDR, and VEGF-RTMII, as shown in FIG. 1.

It is an object of the present invention to provide gene therapy methods to inhibit angiogenesis and growth of solid tumors.

It is also an object of the present invention to utilize a gene or gene fragment of sVEGF-R in gene therapy methods to inhibit angiogenesis and growth of solid tumors.

It is also an object of the present invention to utilize sVEGF-RI in gene therapy methods to inhibit angiogenesis and growth of solid tumors.

It is an object of the present invention to disclose animal models for the determination of efficacy of FLT-1-based constructions for cell delivery and in vivo expression in the mammalian host.

It is an object of the present invention to provide recombinant DNA vectors containing sVEGF-RI constructs for use in gene therapy to locally inhibit angiogenesis in a mammalian host.

BRIEF DESCRIPTION OF THE FIGURES

FIG. 2 shows the nucleotide sequence of which encodes human sFLT-1 [sVEGF-RI] (SEQ ID NO:1).

FIG. 3A and FIG. 3B show the amino acid sequence of human sFLT-1 [sVEGF-RI] (SEQ ID NO:2).

DETAILED DESCRIPTION OF THE INVENTION

Figure 1:
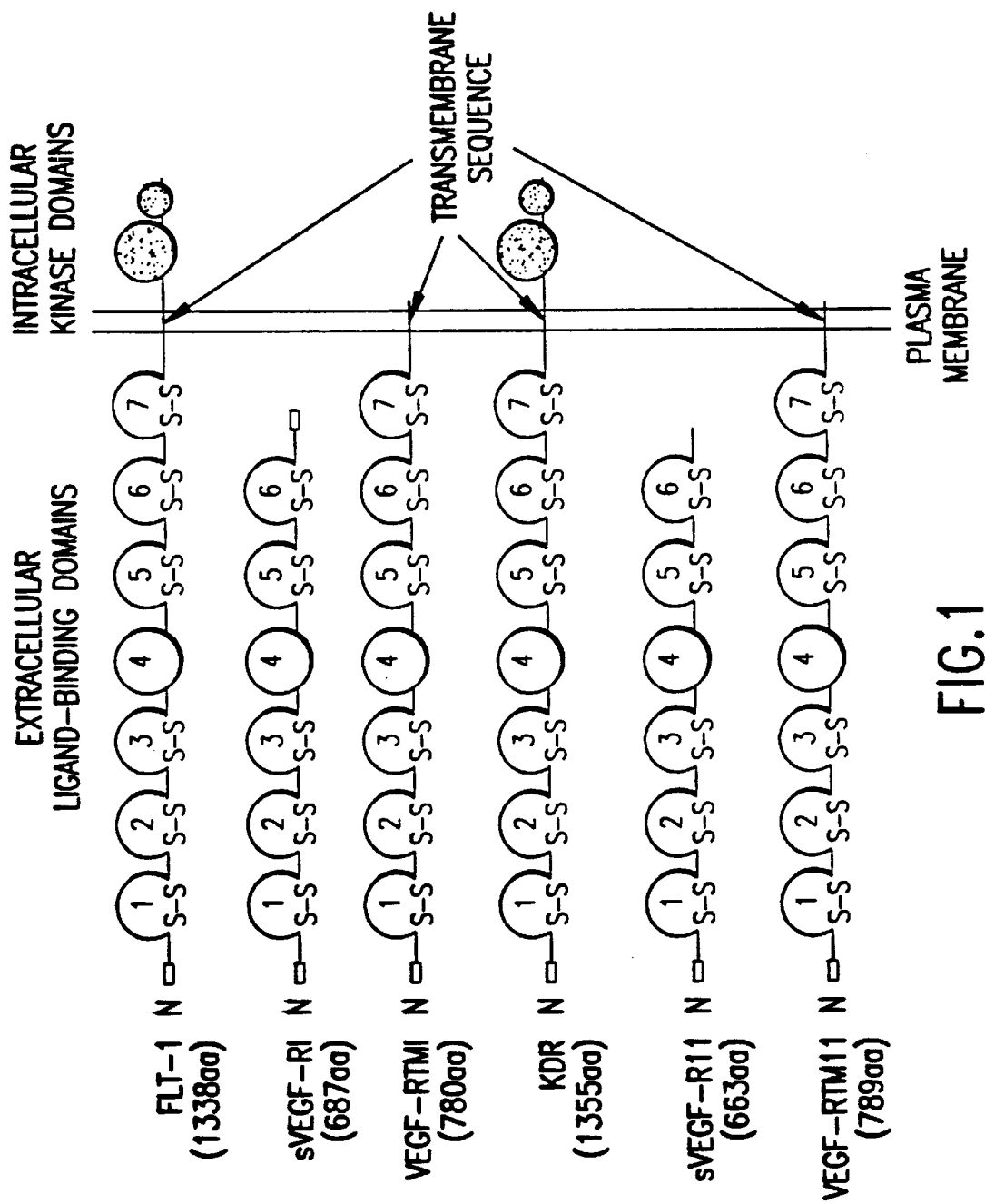
FIG. 1 shows a schematic diagram of full length VEGF-Rs (FLT-1 and KDR), the soluble VEGF receptors (sVEGF-RI and sVEGF-RII) and the soluble receptors containing the C-terminal transmembrane region (sVEGF-RTMI and sVEGF-RTMII), with the protein domains of each.

The present invention relates to methods of gene therapy for inhibiting VEGF-induced angiogenesis associated with diseases and disorders including, but not limited to, solid tumor growth, tumor metastasis, inflammation, psoriasis, rheumatoid arthritis, hemangiomas, angiofibromas, diabetic retinopathy, and macular degeneration. These disorders are related in that VEGF acts as a vascular endothelial cell mitogen and chemotactic agent to stimulate local angiogenesis which in turns exacerbates the condition.

The present invention relates to gene transfer of a DNA vector and concomitant in vivo expression of a soluble form of a VEGF receptor (sVEGF-R) within the mammalian host which binds VEGF or a VEGF homologue in and around the localized site of the disorder. The formation of a sVEGR-R/VEGF complex will inhibit binding of VEGF to the full-length KDR and FLT-1 tyrosine kinase receptors spanning the vascular endothelial cell surface plasma membrane, thus preventing transduction of the mitogenic and other signals stimulating angiogenesis. In addition, expression of sVEGF-R may also impart a therapeutic effect by binding with membrane associated VEGF full-length receptors to form non-functional receptor heterodimers and thereby inhibit the mitogenic activity of VEGF in a dominant negative manner.

A nucleotide sequence encoding a sVEGF-R for inclusion in a gene therapy vector of the present invention may be chosen from a group of genes encoding tyrosine kinase receptors, namely from the group consisting of sflt-1, flt-1, KDR (also denoted flk-1), and flt-4. The resulting DNA fragment encodes a protein or protein fragment which binds VEGF and inhibits formation of a wild-type, functional VEGF-R/VEGF complex.

A preferred application of the present invention relates to methods inhibiting solid tumor angiogenesis, tumor growth and metastasis by utilizing the disclosed gene therapy methodology. In particular, methods are disclosed for inhibition of primary tumor growth and metastasis by gene transfer of a nucleotide sequence encoding sVEGF-R to a mammalian host. The transferred nucleotide sequence transcribes mRNA and expresses sVEGF-R such that sVEGF-R binds to VEGF in extracellular regions adjacent to the primary tumor and vascular endothelial cells and/or heterodimerizes with full-length VEGF-Rs inhibiting their function. Formation of a sVEGF-R/VEGF-R heterodimeric complexes will prevent VEGF-induced dimerization of functional full-length VEGF-Rs, antagonizing receptor transphosphorylation-dependent signal transduction associated with vascular endothelial cell-activation and tumor angiogenesis. In addition, expression of sVEGF-R may also impart a therapeutic effect by binding either with or without VEGFs to form non-functional heterodimers with full-length VEGF-Rs and thereby inhibiting the mitogenic and angiogenic activities of VEGFs in constructing the necessary DNA vector. Restriction endonuclease cleavage sites are identified within the receptor DNA and can be utilized directly to excise the extracellular-encoding portion. In addition, PCR techniques as described above may be utilized to produce the desired portion of DNA. It is readily apparent to those skilled in the art that other techniques, which are standard in the art, may be utilized to produce sVEGF-R molecules in a manner analogous to those described above. Such techniques are found, for example, in Maniatis et al. (1982, Molecular Cloning: A Laboratory Manual; Cold Spring Harbor Laboratory, Cold Spring Harbor, N.Y.).

In a particular embodiment of the present invention a DNA fragment encoding a soluble form of the FLT-1 amino acid sequence (see Shibuya, et al., 1990, *Oncogene* 5: 519–524) is utilized in gene therapy protocols. It will be within the purview of the skilled artisan to generate a sVEGF-R construct which binds to VEGF and inhibits forming a complex with wild-type full-length VEGF-R dimers on the cell surface membrane of vascular endothelial cells. Such a construct may be generated by recombinant DNA techniques known in the art using a DNA fragment encoding a partial or complete amino acid sequence of a FLT receptor. Using recombinant DNA techniques, DNA molecules are constructed which encode at least a portion of the VEGF receptor capable of binding VEGF without stimulating mitogenesis or angiogenesis. As described below, in vivo delivery of a DNA construct encoding sVEGF-R is targeted to cells and tissue which surround the tumor, including but not limited to vascular endothelial cells, muscle cells, adipose cells, as well as tumor cells and surrounding tissues such as muscle tissue and adipose tissue.

The present invention also relates to therapeutic treatment of the metastatic spread of tumors, the principal cause cancer mortality. Tumor cells can metastasize by entry into the circulatory system, transport to distant sites, implantation back into the surrounding tissue and growth. Inhibition of any step in this process would be expected to inhibit the ultimate establishment and growth of metastatic foci. To this end, an additional aspect of the present invention relates to use of the gene therapy constructs of the present invention, including but not limited to sFlt, to the inhibit the metastatic spread of tumors. The significant inhibition of the establishment of HT1080 metastatic lung foci by sflt expression as shown in Example 2 shows that sflt is effective in inhibiting this process. The sflt-1-transfected HT1080 cell tail vein injection experiment monitors implantation and/or growth of circulating tumor cells, two of the crucial steps in metastatic spread. It is envisioned that sflt may decrease the efficiency of tumor cell extravasation out of blood and into surrounding tissue, possibley by inhibiting VEGF-induced vascular permeability which could facilitate cell migration through vessel walls. Additionally, expression of sFlt is expected to arrest neovascular development within metastatic foci thus diminishing their growth and/or viability.

In another particular embodiment of the present invention a DNA fragment encoding the extracellular ligand binding domain and the transmembrane domain of FLT-1 (see FIG. 1) is utilized in gene therapy protocols. Such a DNA construct may be constructed to contain the appropriate wild-type signal sequence such that the proper insertion into the plasma membrane occurs. To this end, it is preferred that viral and non-viral constructs which express VEGF-RTMI (FIG. 1) or a biological equivalent thereof, will be targeted substantially to vascular endothelial cells within the region of the tumor.

In another specific embodiment of the present invention, flt-1 is utilized as a template to generate a mutated version of FLT-1 defective in protein kinase activity. A mutant is this class would possess one or more mutations at or around one or more known active sites for protein kinase activity. In other words, the mutant FLT-1 protein will comprise an extracellular domain, a transmembrane domain, and a mutated intracellular domain. An noted in the previous paragraph regarding delivery of VEGF-RTMI, it is preferred that viral and non-viral constructs which express a mutant FLT-1 be targeted substantially to vascular endothelial cells within the region of the tumor.

An especially preferred template for practicing the present invention is the cDNA encoding a soluble form of FLT-1 (sVEGF-RI), described in Kendall and Thomas (1993, *Proc. Natl. Acad. Sci.* 90: 10705–10709) and U.S. application Ser. No. 08/232,538 which is hereby incorporated by reference. Briefly, a cDNA clone encoding sVEGF-RI was isolated in a two-stage approach employing polymerase chain reaction (PCR) based technology and cDNA library screening. In the first stage, DNA oligonucleotides derived from the extracellular domain sequence information from the known full length FLT, KDR or other VEGF receptor is used to design oligonucleotide primers for the amplification of sVEGF-R-specific DNA fragments. In the second stage, these fragments are cloned to serve as probes for the isolation of complete sVEGF-R cDNA from a commercially available lambda gt10 cDNA library (Clontech) derived from HUVECs (ATCC CRL 1730). This sVEGF-RI cDNA expresses an alternatively spliced form of the FLT-1 precursor mRNA that includes 31 unique amino acid residues at the C-terminal end not found in FLT-1 (see FIG. 2 and SEQ ID NO:1 for nucleotide sequence and FIG. 3 and SEQ ID NO:2 for amino acid sequence). These 31 unique residues are encoded by a intron that is not removed in this alternatively spliced version. The alternatively spliced mRNA is translated into this intron region until the first stop codon is encountered. This especially preferred template (sflt-1 or sVEGF-RI) for a gene therapy vector will express sVEGF-RI in vivo and bind VEGF and/or heterodimerizes with full-length VEGF-Rs (e.g. VEGF-RI/FLT-1 and VEGF-RII/KDR), thus inhibiting tumor angiogenesis.

The cloned sVEGF-RI cDNA obtained through the methods described above may be recombinantly expressed by molecular cloning into an expression vector containing a suitable promoter and other appropriate transcription regulatory elements, and transferred into prokaryotic or eukaryotic host cells to produce recombinant sVEGF-RI. Techniques for such manipulations are fully described in Maniatis, et al.(id.), and are well known in the art.

As noted above, a preferred embodiment of the present invention relates to methods of inhibiting angiogenesis of solid tumors to prevent further tumor growth and eventual metastasis. To this end, any solid tumor or the region surrounding the tumor accessible to gene transfer will be a target for the disclosed therapeutic applications. A sVEGF-R gene or gene fragment, including but not limited to sVEGF-RI and any biologically active truncated version, housed within a recombinant viral- or non-viral-based gene transfer system may be directed to target cells within proximity of the tumor by any number of procedures known in the art, including but not limited to (a) surgical procedures coupled with administration of an effective amount of the DNA to the site in and around the tumor (involving initial removal of a portion or the entire tumor, if possible); (b) injection of the gene transfer vehicle directly into or adjacent to the site of the tumor; and, (c) localized or systemic delivery of the gene transfer vector and/or gene product using techniques known in the art; as listed below.

Therefore, any solid tumor which contains VEGF expressing cells will be a potential target for treatment. Examples, but by no means listed as a limitation, of solid tumors which will be particularly vulnerable to sVEGF-R gene therapy applications are (a) neoplasms of the central nervous system such as, but again not necessarily limited to glioblastomas, astrocytomas, neuroblastomas, meningiomas, ependymomas; (b) cancers of hormone-dependent tissues such as protstate, testicals, uterus, cervix, ovary, mammary carcinomas including but not limited to carcinoma in situ, medullary carcinoma, tubular carcinoma, invasive (infiltrating) carcinomas and mucinous carcinomas; (c) melanomas, including but not limited to cutaneous and ocular melanomas; (d) cancers of the lung which at least include squamous cell carcinoma, spindle carcinoma, small cell carcinoma, adenocarcinoma and large cell carcinoma; and (e) cancers of the gastrointestinal system such as esophageal, stomach, small intestine, colon, colorectal, rectal and anal region which at least include adenocarcinomas of the large bowel.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fungal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant sVEGF-R in mammalian cells. Commercially available mammalian expression vectors which may be suitable for recombinant sVEGF-R expression, include but are not limited to, Commercially available mammalian expression vectors which may be suitable for recombinant sVEGF-R expression, include but are not limited to, pcDNA3.1 (Invitrogen), pBlueBacHis2 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

DNA encoding a sVEGF-R, sVEGF-RI or truncated version thereof may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila, moth, mosquito and armyworm derived cell lines. The expression vector may be introduced into host cells via any one of a number of techniques including but not limited to transformation, transfection, Ad/polylysine DNA complexes, protoplast fusion, and electroporation. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171) and HEK 293 cells. Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

A DNA fragment encoding a sVEGF-R, sVEGF-RI or mutant versions thereof may be delivered either systemically or to target cells in the proximity of a solid tumor of the mammalian host by viral or non-viral based methods. Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picarnovirus vectors; and (i) vaccinia virus vectors. Non-viral methods of delivery include but are not necessarily limited to direct injection of naked DNA, such as a recombinant DNA plasmid expression vector described herein comprising a DNA fragment encoding sVEGF-R, VEGF-RTM, or mutated forms of FLT-1 or KDR.

The present invention therefore relates to non-viral recombinant vectors for delivery to the target hosts. To this end, a preferred recombinant plasmid described herein is pcDNA3/sflt-1. An especially preferred recombinant plasmid of the present invention is pcDNAIAsFLT-1, as decribed in Example Section 5.

A recombinant adenovirus (Ad) system is preferred for delivery and prolonged expression within target cells proximal to a solid tumor. A particularly useful adenovirus system used in the present invention is described in Example 4.

A recombinant Ad/sVEGF-RI is a preferred virus for targeting cells proximal to a solid tumor.

An especially preferred recombinant Ad/sVEGF-RI virus is AdHCMVsFLT-1.

Another especially preferred recombinant Ad/sVEGF-RI virus is AdHCMVI1sFLT .

The recombinant Ad/sVEGF-RI viruses of the present invention, including AdHCMVsFLT-1 and AdHCMVI1sFLT, are preferably administered to the host by direct injection into a solid tumor and/or quiescent tissue proximal to the solid tumor, such as adipose or muscle tissue. It will of course be useful to transfect tumor cells in the region of targeted adipose and muscle tissue. Transient expression of a sVEGF-R or VEGF-RTM in these surrounding cells will result in a local extracellular increase in these proteins and will promote binding with VEGF and full-length VEGF-Rs, thus inhibiting formation of activated full-length VEGF-R dimers.

The recombinant Ad/VEGF-RI viruses of the present invention, including AdHCMVsFLT-1 and AdHCMVI1sFLT, may also be delivered by i.v. injection. A recombinant adenovirus delivered by i.v. injection will preferentially infect hepatocytes when administered intravenously, where expression persists for approximately 3–4 weeks subsequent to the initial infection. Suitable titers will depend on a number of factors, such as the particular vector chosen, the host, strength of promoter used and the severity of the disease being treated.

The skilled artisan may alter the titer of virus administered to the patient, depending upon the method of delivery, size of the tumor and efficiency of expression from the recombinant virus. A dose in the range of $10^9$–$10^{11}$ pfu adenovirus is preferred to treat most primary tumors. The skilled artisan will also realize that the number of viral particles encoding the transgene, whether or not replication competent in a complementing host cell, are a relevant dosing unit. In most Adenovirus constructs, there are 50 to 100-fold more DNA containing particles than pfus.

Non-viral vectors which are also suitable include-DNA-lipid complexes, for example liposome-mediated or ligand/poly-L-Lysine conjugates, such as asialoglyco-protein-mediated delivery systems (see, e.g., Felgner et al., 1994, *J. Biol. Chem.* 269: 2550–2561; Derossi et al., 1995, *Restor. Neurol. Neuros.* 8: 7–10; and Abcallah et al., 1995, *Biol. Cell* 85: 1–7).

There are many embodiments of the instant invention which those skilled in the art can appreciate from the specification. To this end, different transcriptional promoters, terminators, carrier vectors or specific gene sequences may be used successfully.

The present invention provides methods of gene therapy which inhibit tumor angiogenesis in a mammalian host. It will be readily apparent to the skilled artisan that various forms of the nucleotide sequence(s) encoding FLT-1, sVEGF-RTMI, sVEGF-R, sVEGF-RI or any mutated version thereof may be utilized to alter the amino acid sequence of the expressed protein. The altered expressed protein may have an altered amino acid sequence, yet still bind to VEGF and in turn inhibit the molecular cascade required to stimulate tumor angiogenesis. For example, various COOH terminal truncated forms of sVEGF-RI are envisioned in the present invention. It will be of ease for the skilled artisan to generate such altered forms upon review of this specification. Any such truncated version of FLT which is soluble and which binds VEGF, a VEGF homologue and/or FLT-1 or KDR is considered a functional equivalent in light of the teachings of this specification. It is also envisioned, as described in the specification, that membrane bound mutant forms, such as COOH-terminal deletion mutants of FLT-1 and point mutations in the intracellular kinase domain, resulting in a mutant protein substantially defective in protein kinase activity, may be useful as a gene therapy construct for patient delivery and in vivo expression so as to inhibit tumor angiogenesis.

The following examples are provided to illustrate the present invention without, however, limiting the same hereto.

EXAMPLE 1

Isolation of a cDNA Encoding Human sFLT-1

PCR derived products were used as hybridization probes for screening a lambda gt10 cDNA library derived from HUVECs Clontech). Plating and plaque lifts of the library were performed by standard methods (Maniatis, et al., 1982, Molecular Cloning: A Laboratory Manual; Cold Spring Harbor Laboratory, Cold Spring Harbor, N.Y). The probes were random-primed labeled with $^{32}$P-dCTP to high specific activity and a separate screening of the library ($1 \times 10^6$ plaques per screen) was conducted with each probe. The probes were added to hybridization buffer (50% formamide, 5×Denhardts, 6×SSC (1×SSC=0.15 M NaCl, 0.015 M Na$_3$citrate.2H$_2$O, pH 7.0), 0.1% SDS, 100 mg/ml salmon sperm DNA) at $1 \times 10^6$ cpm/ml.

Four positively hybridizing phage were detected using the flt-1-specific probe. These positively hybridizing phage were observed to be less than fill length flt-1.

Two flt-1 cDNA clones of about 2.0 kb and 2.7 kb in length were subcloned into pGEM vectors (Promega) and bi-directionally sequenced in their entirety by the chain termination method (Sanger et al., 1977, *Proc. Natl. Acad. Sci* 74: 5463–5467) and shown to contain a single open reading frame of about 569 amino acids. Sequence analysis demonstrated that a portion of the 5' ft-1 coding region was missing from these clones. The remainder of the 5' end was cloned using PCR and combined with the DNA of the clones lacking the 5' end to yield a single open reading frame encoding about 687 amino acids.

The flt-1-derived sVEGF-RI (sflt-1) cDNA nucleotide sequence and deduced amino acid sequence is shown in FIG. 2 (nucleotide sequence: SEQ ID NO: 1) and FIG. 3 (amino acid sequence: SEQ ID NO: 2). Inspection of the deduced amino acid sequence reveals the presence of a single, large open reading frame of 687 amino acids. By comparison with amino acid sequence of the full length FLT-1 VEGF receptor, 31 amino acids are encoded at the C-terminal end of the sVEGF-RI cDNA which are different from those of FLT-1.

EXAMPLE 2

Inhibition of Tumor Angiogenesis in Mice by Administration of Cells which Transiently Express sVEGF-RI The sVEGF-RI cDNA described in Example 1, cloned in pGEM3z and referred to as psflt-1, was digested with BamHI, purified and ligated into BamHI-digested pcDNA3. The resulting plasmid, pcDNA3/sflt-1 (alternatively referred to as SFLT-1), was verified by restriction mapping as well as DNA sequencing of the 5' and 3' 500 bp of the BamHI insert. The plasmid was transformed into Top10F' *E. coli* and purified using Qiagen mega prep and Qiagen Endotoxin removal kit.

The expression plasmid pcDNA3/sflt-1, was mixed with adenovirus-polylysine (ADPl) and transfected into mouse HT-1080 cells (ATCC CRL 1730). Control transfections were performed in identical fashion using unmodified pcDNA3. HT-1080 cells were transfected when 80% confluent and harvested 16–24 hours for subsequent study.

Cell counting on triplicate wells was performed for 3 time points within 7 days of transfection using trypan blue exclusion and revealed no difference in the growth curves between the two groups.

The harvested cells were injected either subcutaneously or via tail vein in nude mice and nodules were measured on selected days for the subcutaneous nodules. For the tail vein injections two sets of experiments were performed. In the first experiment, the animals were sacrificed prior to the development of nodules but there were detectable differences in the weights of the lungs but the weights were not significantly different. In the second experiment there were definitive differences in the number of nodules per sections with the sflt-1 group having fewer nodules/tissue section.

Figure 4:
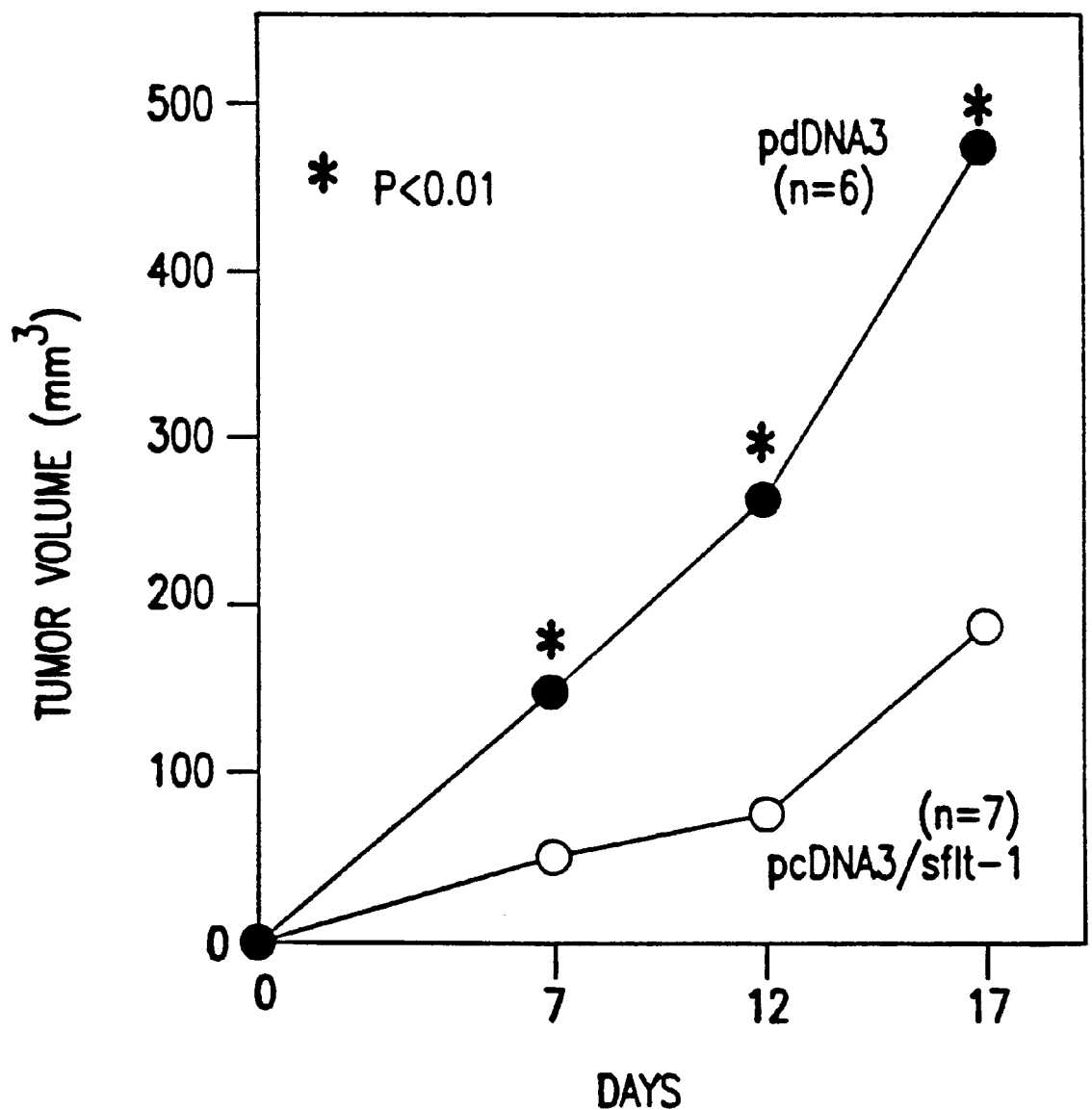
FIG. 4 shows inhibition of tumor nodules grown in nude mice for HT-1080 mouse cells transiently transfected with pcDNA3/sflt-1 (○) or pcDNA3 (●). $3 \times 10^6$ cells were injected at day 0.

Transient transfection with pcDNA3/sflt-1 (n=7), as compared to a pcDNA control (n=6), resulted in slower growing tumor nodules on all days examined (p<0.01). These cells had identical growth rates in vitro over a period of 96 hours. Average nodule volumes for sflt-1 transfected cells were 50 mm$^3$, 75 mm$^3$ and 190 mm$^3$ on days 7, 12, and 17, respectively. In contrast, using control pcDNA3 transfected cells, nodules were 151 mm$^3$ 261 mm$^3$ and 474 mm$^3$ on days 7, 12 and 17. Similarly, mean lung weights were less in animals receiving pcDNA3/sflt-1 (171 mg, n=3) transfected cells by tail vein injection compared to pcDNA3 controls (205 mg, n=3). FIG. 4 shows a marked decrease in tumor volume in nude mice injected with HT-1080 cells which transiently express sVEGF-RI in the form of pcDNA3/sflt-1.

A second study designed to investigate the ability of sFLT-based gene therapy to be applied to treatment of tumor metastasis yielded similar results. HT-1080 cells were transiently transfected with pcDNA3 or pcDNA3/sflt-1. 4×10$^6$ cells were injected at day 0 via the tail vein of each mouse. The animals were sacrificed after one month and the lungs were extracted, weighed, and examined histologically for tumor burden. Lung histology performed on animals receiving intravenously injected tumors revealed a striking difference between the two groups. pcDNA3 transfected cells were associated with pulmonary intramural tumor spread, massive parenchymal edema and mononuclear infiltrate 20 days after intravenous injection of tumor cells. In contrast, pcDNA3/sflt-1 transfected cells were associated with rare tumor foci, the absence of edema and almost normal lung parenchyma histology. Eight of 9 animals injected with HT-1080 cells transiently expressing sVEGF-RI were clear of tumor growth. Conversely, HT-1080 tumor cells transfected with the pcDNA3 control plasmid showed 2 of 9 without tumor growth while 7 of 9 formed lung nodules. This data shows that sFLT-based gene therapy applications may be utilized to treat tumor metastasis.

Third, a syngeneic model was examined. Pooled clones were generated for either pcDNA3 or pcDNA3/sflt-1 in GL261 mouse glioma cells. Cell counting of the cells grown in culture revealed no differences between the groups. All 3 pcDNA3 animals grew large tumors after approximately one month. Two of 3 in the sFLT-1 group were tumor free. The third had formed a very small tumor. The histopathology differed but all tumors had a clear malignant appearance.

EXAMPLE 3

Figure 5:
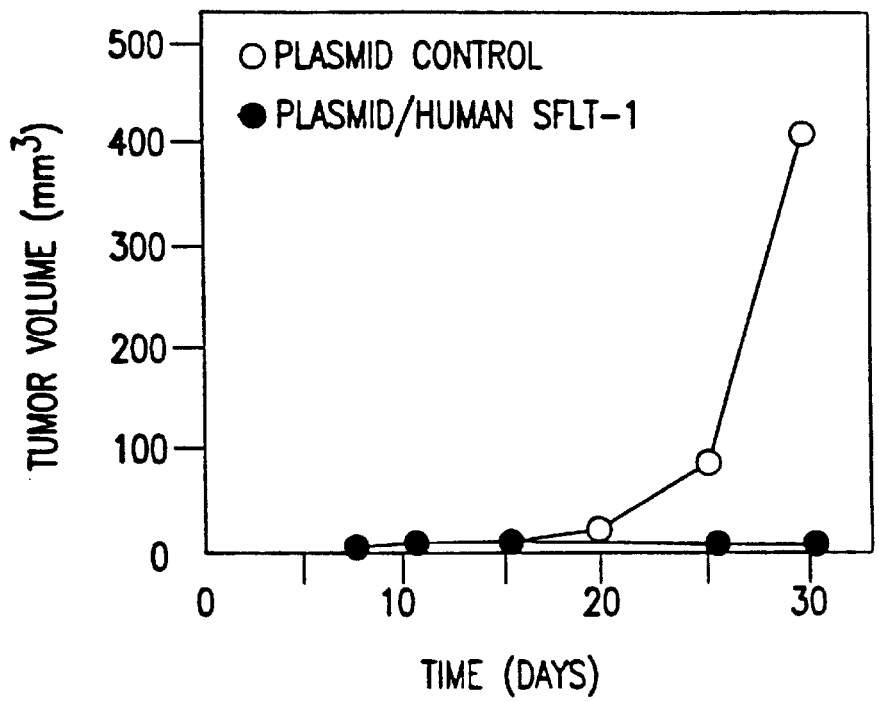
FIG. 5 shows inhibition of tumor nodules grown in nude mice for HT-1080 mouse cells stably transfected with pcDNA3/sflt-1 (●) or pcDNA3 (○).

Inhibiton of Tumor Angiogenesis in Mice by Administration of Cells Stably Transfected with a cDNA Fragment Encoding sVEGF-RI The study described in Example 2 was repeated with HT-1080 cells stably transfected with either the pcDNA3 control of pcDNA3/sflt-1. FIG. 5 shows a virtually complete inhibition of tumor growth compared to the additional data generated with transiently transfected tumor cells.

Figure 6:
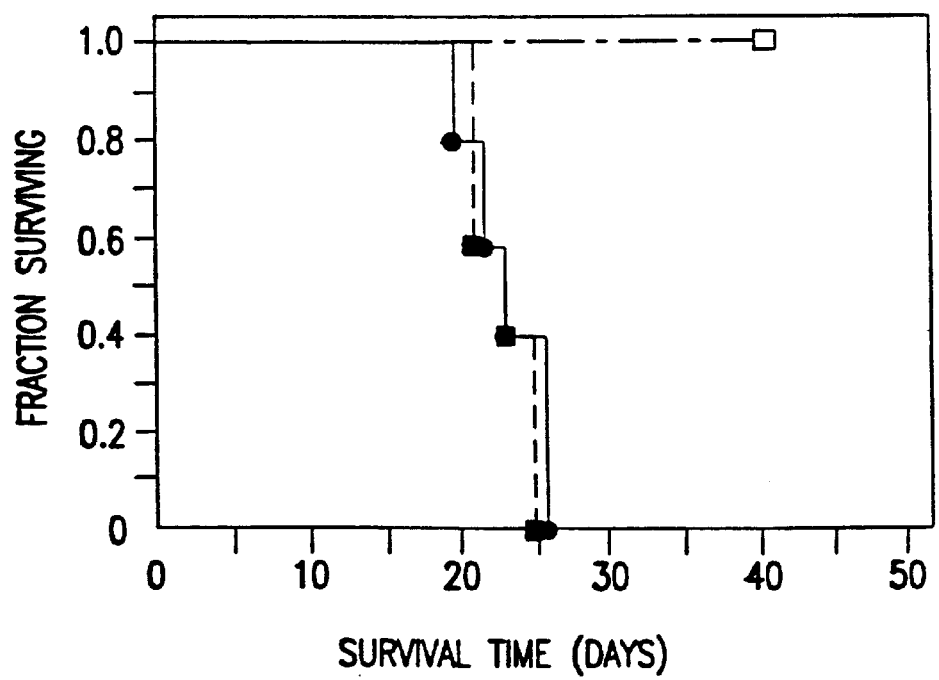
FIG. 6 shows the survival plot of scid mice injected with (a) D-54MG human glioblastoma cells stably transfected with pcDNA 3 (■); (b) D-54MG human glioblastoma cells stably transfected with pcDNA-sflt-1 (□); and (c) untransfected D-54MG human glioblastoma cells (▥).
Figure 7:
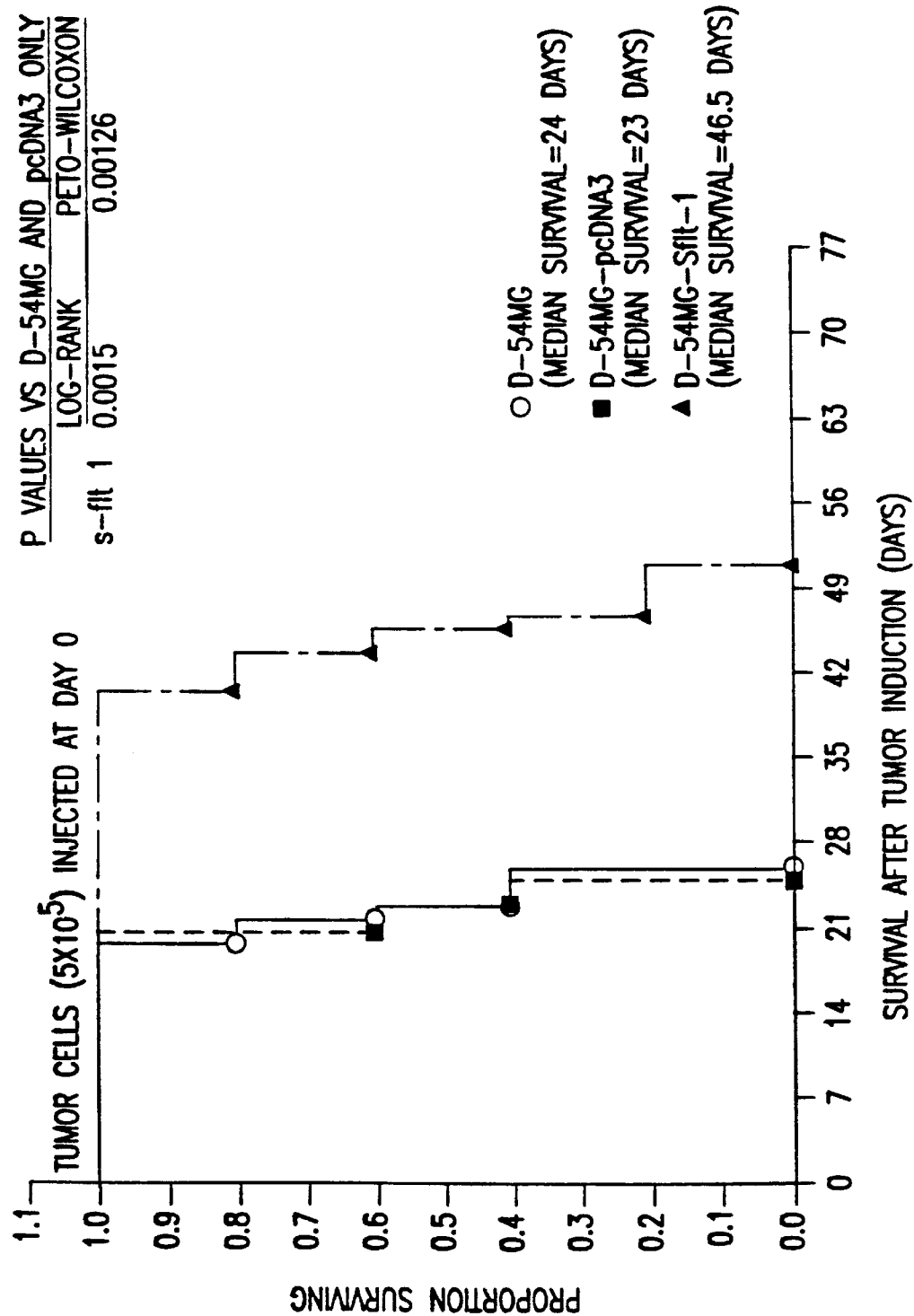
FIG. 7 shows additional data points from the experiment detailed in FIG. 6, namely that a CB-17 scid-mouse human-glioma model was used to asses the effect of stable sflt-1 expression on tumor growth and survival. (■)D-54MG human glioblastoma cells stably transfected with pcDNA3; (b) D-54MG human glioblastoma cells stably transfected with pcDNA-sflt-1 (▲); and (c) untransfected D-54MG human glioblastoma cells (○).

To determine the effects of sVEGF-RI on animals survival, the human glioma cell line D-54MG was stably transfected with pcDNA3/psflt-1 or a pcDNA3 control. Clones were pooled and the same number of cells were injected intracranially using a mouse stereotactic device with skull sutures as landmarks. The model has previously been determined to have reliable survival characteristics. Animals were treated identically post-operatively. FIG. 6 shows that mice injected with an untransfected control died by day 26, mice injected with pcDNA3 transfected control cells died by day 25, wherein all mice which received pcDNA3/sVEGF-R transfected cells were alive at day 41. FIG. 7 shows extended data points from this experiment, showing that the mean survival for D-54MG cells transfected with pcDNA3/sflt-1 was 46.5 days. As noted earlier in this paragraph, D54-MG human glioma cells were transfected with pcDNA3/sflt-1 or pcDNA3 using AdpL transfection. The cells were subsequently propagated in complete medium containing 400 µg/mL of G418 antibiotic (Gibco BRL, Grand Island, N.Y.) for one month to select for a population of clones that contained the pcDNA3/sflt-1 or pcDNA3 plasmid. The selected cells, representing a population of pooled clones were then harvested using trypsin/

EDTA solution (Gibco) and counted using a hemacytometer with trypan blue exclusion. The cells were resuspended to a final concentration of $10^7$ cells/100 µL in serum-free DMEM/F12 containing 5% methylcellulose as a vehicle to enhance cell viability. A midline scalp incision was made, followed by a 0.5 mm burr hole 1.5–2.0 mm to the right of the midline and 0.5–1.0 mm posterior to the coronal suture. The cells were loaded into a 100 µL microsyringe and 5 µL was injected sterotactically. A 30 gauge needle mounted on the microsyringe was inserted vertically through the burr hole to a depth of 2.5 mm. Forty-five to sixty seconds after injection, the needle was slowly withdrawn and the incision closed with 9 mm Michel wound clips. Mice were returned to sterile microisolator polycarbonate cages, placed over a heating pad until recovery, and provided autoclaved lab chow and sterile water ad libitum. Animals were assessed twice daily for survival. These results demonstrate that sFLT-1 animals survived longer than historical controls and subsequent controls.

EXAMPLE 4

Construction of AdHCMVsFLT-1

Several systems have been developed for the construction of helper-independent adenovirus (Ad) vectors and have been recently been reviewed by Graham and Prevec (1995, *Mol. Biotech.* 3: 207–220) and Hitt et al. (1995, Techniques for human adenovirus vector construction and characterization, In *Methods in Molecular Genetics, Volume 7. Molecular Virology Techniques Part B*, ed. Kenneth W. Adolph, Academic Press, Inc. Orlando, Fla.). All of these systems involve cloning the transgene of interest (coding region flanked by appropriate regulatory sequences) into a shuttle plasmid in which it is flanked by Ad sequences homologous to the region of the viral genome into which the transgene will be introduced. The DNA from the shuttle plasmid is then rescued into virus by either direct ligation in vitro followed by transfection or by in vivo homologous recombination following transfection into 293 cells.

E1 shuttle plasmids have been developed for the rescue of inserts into the E1 region. These plasmids contain the left 16% of the Ad genome with a deletion of E1 sequences and cloning sites into which the transgene is introduced. If convenient restriction sites are available in the vector backbone, direct ligation of the shuttle plasmid to purified viral DNA can be performed in vitro followed by transfection into 293 cells to generate infectious virus. This method although efficient can require extensive screening if the viral DNA is not completely restricted and in many cases is not practical due to the lack of unique correctly positioned restriction sites. For these reasons many protocols rely on in vivo homologous recombination to generate infectious virus. To construct a virus by homologous recombination the shuttle plasmid can be transfected into 293 cells with purified viral DNA that has been restricted in the left end or with viral DNA contained in a second plasmid. As with direct ligation the use of purified viral DNA sometimes requires extensive screening to obtain the desired vector because of the regeneration of parental virus and for this reason plasmid systems are more desirable. A number of plasmid systems have been developed for rescuing inserts into E1 (McGrory et al., 1988, *Virology* 163: 614–6170) or E3 (Ghosh-Choudhury, et al., 1986, *Gene* 50: 161–171; Mittal, et al., 1993, *Virus Res.* 28: 67–90) or both (Bett et al., 1994, *Proc. Natl. Acad. Sci. USA* 91: 8802–8806) regions.

The steps involved in the construction of the helper independent Ad vectors expressing sFLT-1 are outlined below. All steps involve the use of standard protocols for generating adenovirus vectors (Hitt, et al., 1995, *In Methods in Molecular Genetics, Volume 7. Molecular Virology Techniques Part B*, ed. Kenneth W. Adolph, Academic Press, Inc. Orlando, Fla.). The coding sequences for sFLT were obtained from plasmid psflt-1 by BamHI digestion and inserted into the BamHI site in the polycloning region of E1 shuttle plasmid pΔE1sp1HCMV-BGHpA, generating pHCMVsFLT-1. pΔE1sp1HCMV-BGHpA contains Ad5 sequences from bp 1 to 341 and bp 3524 to 5790 with a promoter cassette consisting of the HCMV promoter, a polycloning region and the Bovine growth hormone polyadenylation signal inserted in the E1 anti parallel orientation between Ad5 bp 341 and bp 3524. pHCMVsFLT-1 was then cotransfected into 293 cells with Ad genome plasmid pJM17 (McGrory, et al., 1988, *Virology* 163:614–617) and virus AdHCMVsFLT-1 was generated by in vivo recombination between the plasmids. pJM17 contains essentially the entire Ad genome but is non infectious in single transfections of 293 cells since it contains an insertion of a pBR322 derivative at bp 1339 in Ad5 sequences which makes the resulting viral genome too large to package. In vivo recombination between pJM17 and pHCMVsFLT-1 generates a vector of a packagable size containing the sFLT-1 expression cassette in the E1 region.

An additional recombinant adenoviral virus is also disclosed. It is essentially the same as the vector described above but utilizes a slightly different HCMV promoter segment consisting of the HCMV promoter and first intron (Intron A). This construct increases expression levels within the mammalian host. To construct this vector sFLT-1 coding sequences were obtained from plasmid pHCMVsFLT-1 (described above) by digestion with KpnI and EcoRI. The sFLT-1 fragment was then inserted into the KpnI and EcoRI sites in E1 shuttle plasmid pHCMVI1-BGHpA, generating pHCMVI1sFLT-1. pHCMVI1sFLT-1 has been cotransfected into 293 cells with Ad genome plasmid pJM17. Alternatively, pHCMVI1sFLT-1 was digested with PacI and ligated with purified viral DNA from the virus AdDE1PacIE3 also digested with PacI. Following the transfection of the ligation products into 293 cells viral plaques were screened to obtain the vector AdHCMVI1sFLT-1.

EXAMPLE 5

Stable Transfection of Human HT1080 Fibrosarcoma Cells with sFlt-1 Inhibits Solid Tumor Growth Generation of sFlt-1 plasmid—An additional plasmid (pcDNAIAsFLT-1) was constructed that contained the HCMV Intron-A upstream to the sflt-1 cDNA in order to generate HT-1080 clones that secrete increased amounts of sflt-1. This intron has been demonstrated in previous studies to enhance gene expression by 10–100 fold above plasmids containing the HCMV early promoter alone. For the construction of pcDNAIAsFLT-1, pcDNA3 was digested with NruI and KpnI (to remove the HCMV promoter) and ligated with the MscI/KpnI fragment from plasmid pVIJNS-MCS (containing the HCMV promoter and Intron A), generating pcDNAINTA. pcDNAINTA was then digested with KpnI and EcoRI and ligated to a KpnI/EcoRI fragment containing the sFLT-1 coding sequences, generating pcDNAIAsFLT-1.

Selection of HT1080 clones stably transfected with pcDNAIAsFLT-1 and expressing sFlt-1—Human fibrosarcoma HT1080 tumor cells (Rasheed et al., 1974, *Cancer* 33:1027–1033) were transfected with the plasmid (pcDNAIAsFLT-1) containing the human sFlt-1 gene under the control of the RCMV promoter containing the first HCMV intron and the selectable G418 drug resistance gene. Pooled stably transfected HT1080 cells were plated in 100 cm dishes at a density of 10 and 100 cells/plate. The cells were grown in DMEM supplemented medium [Dulbecco's Modified Eagle Medium/F-12 (DMEM), GIBCOBRL (Cat# 11331–030), 10% fetal bovine serum, (GIBCOBRL Cat# 16000–028) and 1×penicillin-streptomycin, (GIBCOBRL Cat# 15070–063)] with 500 µg/ml of G418 (GIBCOBRL Cat# 10131–035). The medium was replaced every other day until individual colonies grew to diameters of approximately 2.5 mm. Isolated colonies were treated with trypsin (GIBCOBRL Cat# 25200–056), transferred to 24 well plates and grown to confluence. One ml of medium was removed and tested for VEGF binding activity. The stable clone chosen for further studies had similar growth rates in vitro compared to both untransfected cells and cells transfected with pCDNA3, with cell division occuring approximately every 48 hours.

VEGF Binding Protocol—Heparin-Sepharose CL-6B (Pharmacia Cat# 17-0467-01) was washed 3 times with phosphate buffered saline [PBS] (GIBCOBRL Cat# 20012–027), and resuspended in an equal volume of PBS. One ml of conditioned medium was removed from each well, mixed with 50 µl of the heparin-Sepharose CL-6B slurry and incubated overnight at 4° C. with constant mixing. The heparin-Sepharose beads were pelleted by centrifugation (10,000×g for 2 min) and washed 3 times with PBS. Bound protein was eluted with 40 µPl of PBS containing 1.2 M NaCl. A 10 µl aliquot was removed and added to 10 µl of DMEM/0.2% gelatin, 1 µl of $^{125}$I-VEGF (Amersham Cat# IM 274; 100,000 cpm/µl) was added and incubated for 20 min at room temperature. Two µl of 10 mM $BS^3$ bis (sulfosuccinimidyl) suberate [$BS^3$], (Pierce Cat# 21579 G) was added to the reaction and incubated for an additional 15 min at room temperature. The crosslinking reaction was stopped by the addition of 20 µl of 2×Laemmli sample buffer (BioRad Cat# 161–0737). Crosslinked complexes were separated by SDS/7.5% PAGE and visualized by autoradiography.

Figure 8:
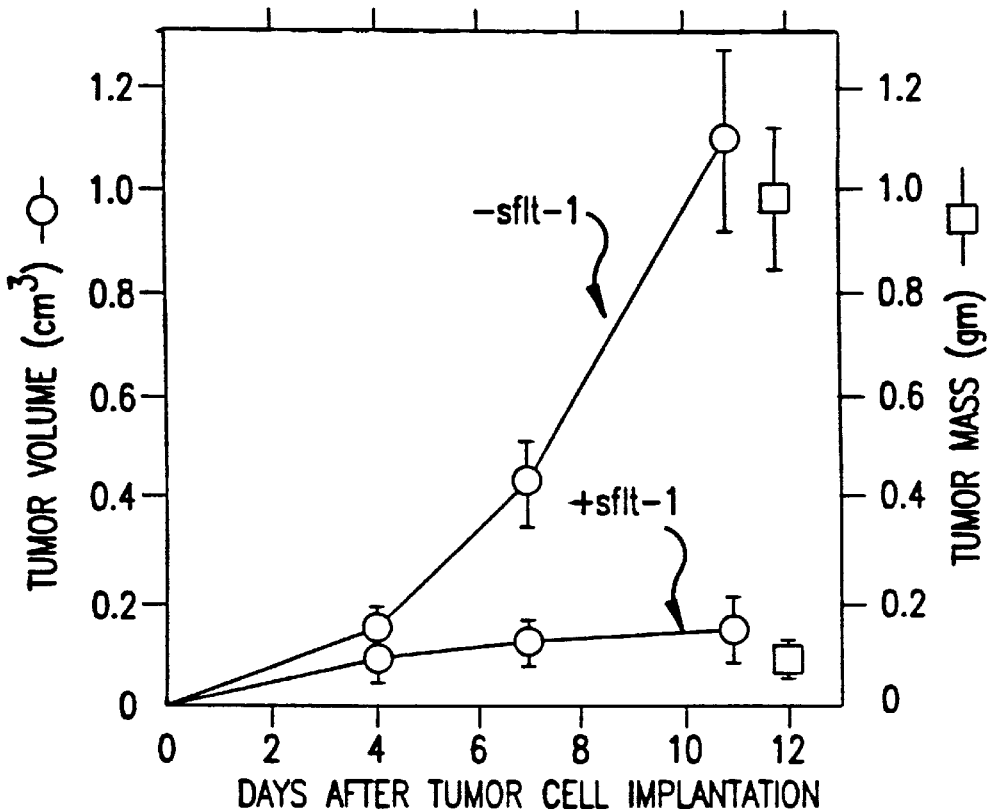
FIG. 8 shows that tumor growth in mice as measured by average volume and mass (±SD) was significantly inhibited by expression of the sflt-1 gene (1-tailed Student's t-test, $p<0.0001$ for comparison of masses) subcloned into pCDNA1A3, resulting in pcDNAIAsFLT-1.

Preparation of selected clones for the tumor growth study—Cells were plated in T-75 flasks and grown to confluence in DMEM supplemented medium. Cells were washed with PBS and trypsinized in 2 ml. Trypsinization was stopped by the addition of 8 ml DMEM supplemented medium and the detached cells were removed and counted. The cells were pelleted by centrifugation (1000 rpm in a Sorvall 6000B table top centrifuge) for 5 min and resuspended in PBS with calcium and magnesium at a final concentration of $1.0 \times 10^7$ cells/ml and 0.5 ml of cells was injected subcutaneously into mice. Results—HT-1080 cells ($0.5 \times 10^6$ cells/0.5 ml) stably transfected with either control plasmid or plasmid encoding sflt-1 [pcDNAIAsFLT-1] (n=10/group) that was cloned and selected for high sflt-1 expression were injected subcutaneously into Balb/c nu/nu female mice (Charles River Laboratories). Tumor length and width were measured as a function of time and used to calculate tumor volume by the equation:

Volume=4/3·p·((length/2)(width/2)(length+width)/4), which estimates the volume of half a prolate ellipsoid assuming that the height is the average of the length and width. On day 12 after implantation tumor ulceration was visible so the tumors were removed and weighed; expression of sFlt-1 caused a 93% reduction in tumor mass. As shown in FIG. 8, tumor growth as measured by average volume and mass (±SD) were significantly inhibited by expression of the sflt-1 gene (1-tailed Student's t-test, p<0.0001 for comparison of masses).

EXAMPLE 6

Infection of Human HT1080 Fibrosarcoma Cells with Replication-Defective Adenovirus Expressing Human sFlt-1 Inhibits Tumor Growth Generation of sFlt-1 adenoviral constructs are as described in Example Section 4.

Adenoviral infection of HT1080 cells in vitro and implantation in vivo—Cells were plated in T-75 flasks and grown to confluence in DMEM supplemented medium. One flask of cells was trypsinized (2 ml), the cells were removed and resuspended in DMEM supplemented medium and counted to determine the number of cells/plate. Growth medium was removed from flasks and the attached cells were washed with PBS containing calcium and magnesium. Either control adenovirus or adenovirus expressing human sFlt-1 under control of HCMV/intron A were added to flasks at an multiplicity of infection of 20 virus pfu (plaque forming units)/cell in 2 ml of PBS with calcium and magnesium and incubated for 1 hr at 37° C. The virus was removed and the cells were incubated in a humidified incubator wi 5% $CO_2$ at 37° C. for and additional 24 hr. Cells were washed with PBS and trypsinized with 2 ml of trypsin. Trypsinization was stopped by the addition of DMEM supplemented medium and the detached cells were removed and counted. The cells were pelleted by centrifugation (1000 rpm in a Sorvall 6000B table top centrifuge) for 5 min and resuspended in PBS with calcium and magnesium at a final concentration of $1.0 \times 10^7$ cells/ml and 0.5 ml of cells was injected subcutaneously into 6–8 week old Balb/c nu/nu female mice.

Figure 9:
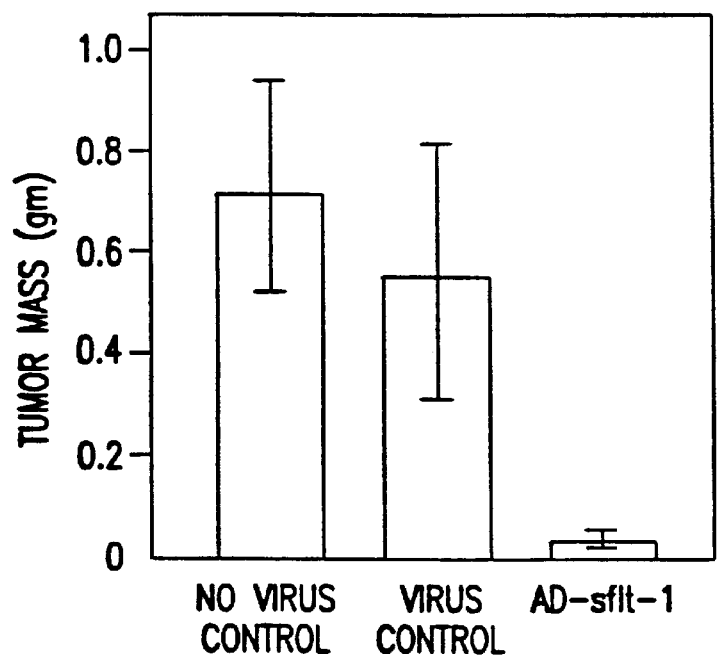
FIG. 9 shows that the tumor masses in mice of sFlt-1 expressing cells were significantly smaller than either the adenovirus treated control cells (p=0.035) or the no virus treated control cells (p=0.007) using the appropriate 1-tailed Student's t-test.

Results—Tumor cells that were exposed to either no virus, a control adenoviris or adenovirus expressing sFlt-1 under control of the HCMV/intron A promoter [AdHCMVI1sflt-1] (n=5/group) were allowed to grow subcutaneously in nude mice. After 11 days of in vivo growth the skin over the tumor began to ulcerate in control animals so the tumors were removed from all animals and weighed. The mean group tumor masses ±SEMs are shown in FIG. 9.

What is claimed is:

1. A method of determining efficacy of inhibiting tumor angiogenesis, which comprises:

(a) transfecting cultured tumor cells with a recombinant vector expressing a soluble FLT-1 protein;
   (b) injecting said transfected tumor cells into a mouse;
   (c) sacrificing said mouse after an interval allowing for tumor growth within said mouse; and,
   (d) observing formation of tumor nodules in said mouse as compared to a mouse injected with tumor cells transfected with vector alone or untransfected tumor cells.

2. The method of claim 1 wherein the recombinant vector of step (a) comprises the nucleotide sequence as set forth in SEQ ID NO:1.

3. The method of claim 3 wherein the recombinant vector is an adenovirus vector.

4. The method of claim 1 wherein the recombinant vector is a DNA plasmid vector.

5. The method of claim 3 wherein the recombinant vector of step (a) comprises the nucleotide sequence as set forth in SEQ ID NO:1.

6. The method of claim 4 wherein the recombinant vector of step(a) comprises the nucleotide sequence as set forth in SEQ ID NO:1.

* * * * *